Oct. 19, 1971 C. H. FISCHER Plant Pat. 3,079
GLADIOLUS PLANT
Filed Aug. 6, 1969
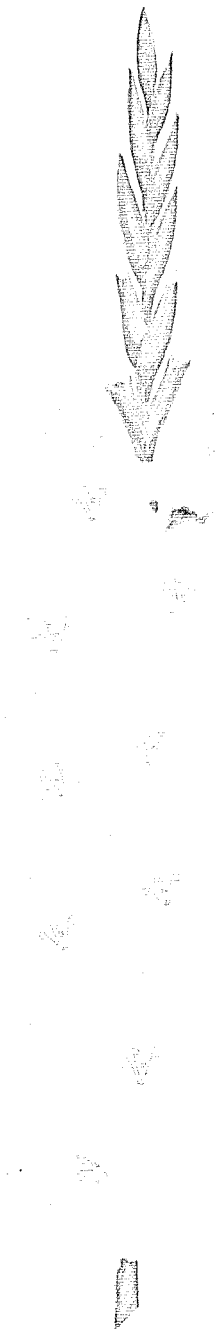
INVENTOR
Carl H. Fischer
By: Lamont Johnston
ATTORNEY United States Patent Office Plant Pat. 3,079
Patented Oct. 19, 1971

3,079
GLADIOLUS PLANT

Carl H. Fischer, St. Charles, Minn. assignor to
Selected Glads, Inc., Albany, Ind.

Filed Aug. 6, 1969, Ser. No. 848,122
Int. Cl. A01h *5/00*
U.S. Cl. Plt.—85 1 Claim My present invention relates to a new and improved variety of gladiolus plant and is notable particularly for its rugged plant, consistent performance, novel blend of blossom colors, and ability to open many florets at once. I have identified this variety as Seedling #482–62 in my breeding work and its cultivar name is "Apollo."

To the best of my knowledge, this variety is the result of a cross between two unidentified seedlings. Hand cross pollination was done by me in my field at St. Charles, Minn., but no precaution was taken to prevent admixture of the other varieties by bees and insects.

This new variety has been asexually reproduced by me in Minnesota by natural increase from cormels and its characteristics have proven to be permanently fixed after several generations of growing.

The illustration, made a part of this application, shows a single bloom spike, reduced in size, and is as nearly true to color as it is possible to depict. It shows the unusual variation of color, the form and placement.

In the following detailed description, color plate references are to "The Horticultural Colour Chart," by The British Colour Council. Where there are other references to color, the ordinary dictionary meanings of the terms are intended.

*The plant*

Growth: Extremely rugged, growing to 55 inches in height overall. Average propagator.

Blooming: Comes into bloom in about 85 days from large bulbs.

Stems: Diameter of the stem is ½ inch. Always sturdy, seldom crooks. Stem is deep purple above the bulb.

Foliage: Healthy green leaves, strongly ribbed and upright, droops very slightly; 1¼ inches across. Narrow plant is 40 inches tall, excluding the flower spike.

Disease Resistance: Exceptionally disease resistant.

Corms: Round, plump and smooth; excellent bulb. Straw colored husk. Flesh is ivory.

*The flower*

Spike: Flowerhead is 24 to 28 inches high, with 18 to 20 buds and 10 to 12 florets open at one time.

Bud: Size: Opening bud is 2 inches long. Opening: 5 to 6 show color at once.

Flower: Arrangement: Semi-formal to formal; almost never misplaces.

*Size.*—Individual florets are 4¼ to 4½ inches across.

*Form.*—Round, wide open, ruffled and slightly needlepointed.

*Keeping qualities.*—Opens well but color fades and changes as flowers open up the stem.

Petals:

*Shape.*—Round, ruffled at edges, upper petals have strong mid-ribs.

*Size.*—Outer petals are 1½ inches across; lip, 1 inch.

*Aspect.*—Average substance. Surface smooth on inner florets; outer area ruffled.

*Fragrance.*—None.

*Color.*—Chinese Coral 614/2; fades to 614/3; deeper in throat. Color of throat, Aureolin 3/1. Two light purple spots at base of upper petal where upper petal is attached to calyx.

Reproductive organs: Stamens.—Purple lavender tips. Pistil—Cream.

*Comparisons*

My new variety resembles All Ruffles (unpatented) more than any other variety but differs from it principally as follows:

(1) My new variety is taller.
(2) My variety has a more contrasty blotch.
(3) My variety has more blooms open at once.
(4) My variety is a better grower from bulblets.

Having thus disclosed my invention, I claim:

1. The new and distinct variety of gladiolus plant, substantially as herein shown and described, characterized by its rugged plant, consistent performance, novel blend of blossom colors, and ability to open many florets at once.

No references cited.

ROBERT E. BAGWILL, Primary Examiner